United States Patent [19]

Williamson

[11] 3,930,493

[45] Jan. 6, 1976

[54] INTRAVASCULAR LIQUID VELOCITY SENSING METHOD USING A POLAROGRAPHIC ELECTRODE

[75] Inventor: Donald E. Williamson, Miami, Fla.

[73] Assignee: Cordis Corporation, Miami, Fla.

[22] Filed: Oct. 7, 1974

[21] Appl. No.: 512,477

Related U.S. Application Data

[63] Continuation of Ser. No. 435,638, Jan. 23, 1974, abandoned, which is a continuation of Ser. No. 228,918, Feb. 24, 1972, abandoned.

[52] U.S. Cl............ 128/2.05 F; 128/2 E; 73/194 F; 204/195 B
[51] Int. Cl.².......................................... A61B 5/02
[58] Field of Search..... 128/2.05 F, 2 L, 2 E, 2.1 E, 128/2.05 D; 73/194 F, 194 E; 324/29 R, 30 R; 204/195 B, 195 P, 195 R, 195 L, 195 M

[56] References Cited
UNITED STATES PATENTS

| | | | |
|---|---|---|---|
| 1,411,796 | 4/1922 | Meyer | 73/194 F |
| 3,242,729 | 3/1966 | Keller | 128/205 F |
| 3,450,984 | 6/1969 | Holmes | 73/194 E |

*Primary Examiner*—Richard A. Gaudet
*Assistant Examiner*—Lee S. Cohen
*Attorney, Agent, or Firm*—Kenway & Jenney

[57] ABSTRACT

The linear flow rate of a liquid containing dissolved oxygen, such as blood, can be determined by means of an electrode assembly having exposed to the liquid a relatively large polarographically active cathode and spaced therefrom a reference anode. With an applied energizing voltage of about 0.4–0.9 volts a current plateau is reached which is proportional to fluid flow rate. As the device is also sensitive to oxygen content, compensation can be measured by providing on the assembly an oxygen sensing membrane covered polarographic electrode pair of the Clark type.

1 Claim, 2 Drawing Figures

INTRAVASCULAR LIQUID VELOCITY SENSING METHOD USING A POLAROGRAPHIC ELECTRODE

This is a continuation of application Ser. No. 435,638, filed Jan. 23, 1974, now abandoned; which is a continuation of application Ser. No. 228,918 filed Feb. 24, 1972, now abandoned.

INTRODUCTION

This invention relates to the measurement of liquid linear flow rates and provides an electrode assembly useful for instance for measuring the flow rate of blood within the cardiovascular system.

BACKGROUND OF THE INVENTION

It is known that the oxygen content of liquids and gases can be determined by polarographic measurements in which oxygen is reduced at a polarographically active cathode. Measurement of the cathode current provides means for determining the partial pressure of oxygen($pO_2$) in the fluid. Ordinarily the measurement requires a cathode area small enough that the current is unaffected by the linear flow rate of the liquid. With large cathodes spurious results occur at low flow velocity because the liquid adjacent to the cathode surface becomes so depleted of oxygen that the reduction current does not depend entirely on the oxygen concentration, but also on the rate at which the liquid moves to and from the surface. As the flow velocity increases the current also increases to a plateau level, which is a function of the $pO_2$.

BRIEF DESCRIPTION OF THE INVENTION

It has now been ascertained that flow rate of the liquid can be determined with the use of a large polarographic cathode by measuring the current at certain voltage conditions.

The cathode current will increase as the voltage is increased, reach a brief plateau where no further increase occurs with incremental voltage rise, and then continue to increase beyond the plateau. The measurement of the current at or near the plateau can be correlated to and utilized to determine the linear flow rate of the liquid.

A criterion for the measurement of intravascular blood flow is a cathode having a surface area larger than 8 sq. mm. Accordingly the invention in its preferred embodiment comprises a tubular body, e.g., an intravascular cathode, of insulating material, on which is mounted a polarographic cathode, of, e.g., gold or platinum, having a surface area in excess of 8 sq. mm. Spaced from the cathode on the catheter body is a reference anode for instance silver/silver chloride. Separate conductors make connections with the two electrodes and extend through the lumen of the catheter so that appropriate electrical contact can be made at the proximal end outside of the subject body.

In a preferred embodiment, which provides for compensation of the $pO_2$ of the fluid, a separate membrane covered (Clark) polarographic couple is also provided. Conveniently this is located at the distal tip of the catheter body and comprises a small polarographic cathode surrounded by the reference anode, e.g., silver/silver chloride. A membrane of polyethylene or Teflon surrounds both cathode and anode and retains a thin film of aqueous electrolyte in contact with the electrodes.

DESCRIPTION OF DRAWINGS

The invention is described below with reference to a presently preferred embodiment illustrated in the drawings in which.

DESCRIPTION OF THE PREFERRED EMBODIMENT

Figure 1:
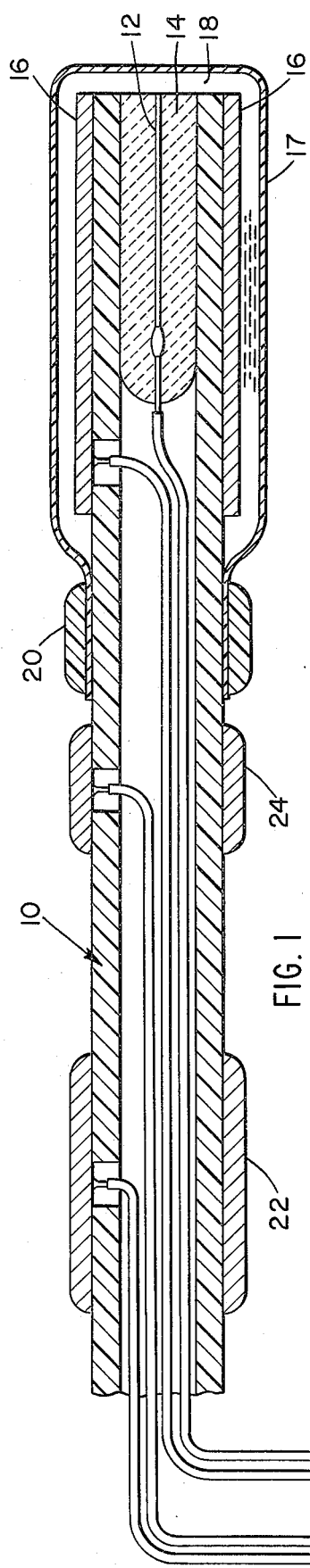
FIG. 1 is a longitudinal cross-sectional view of a flow rate assembly embodying this invention.

The preferred embodiment illustrated in FIG. 1 utilizes a catheter body 10, which may be of conventional construction, preferrably of an insulating material such as an elastomeric polyurethane or polyethelyne. The distal tip of the catheter carries the $pO_2$ sensing electrode arrangement, namely a cathode 12 of, for instance, 0.001 inch diameter platinum wire, mounted in a bead 14 of an insulating material such as epoxy resin glass or the like. The cathode 12 extends through the bead and is exposed at the outside face. An anode 16 surrounds the cathode; it is conveniently mounted as a band surrounding the tip of the catheter body 10. The anode 16 and cathode 12 are covered by an oxygen permeable membrane 17, which also retains a thin film of electrolyte 18. Typically the membrane will be Teflon or polyethelene and the electrolyte will be isotonic aqueous potassium chloride. The membrane with the contained electrolyte is conveniently held in place by an elastic ring 20 against the catheter body.

Flow rate sensing is accomplished by a separate polarographic cathode-anode arrangement. The cathode 22 is in the form of a platinum ring surrounding the cathode body and presenting a surface area about 8–10 sq. mm. or more. Adjacent to the cathode 22 is an anode 24, of for instance silver/silver chloride also in the form of a band surrounding the cathode body. Separate conductor leads, four in number connect with the several electrodes and they extend the length of the catheter body, emerging at its proximal end.

In medical applications the catheter will be inserted into the blood stream and appropriate sensing voltages applied to the various electrodes typically 0.4–0.9 volts will be applied to the flow rate sensing cathode-anode pair 22, 24 and 0.6 volts to the $pO_2$ sensing cathode-anode pair 12, 16 and their respective currents measured. The current measured for the $pO_2$ sensing cathode-anode pair 12, 16 will indicate the oxygen content of the blood while the current measured for the flow rate sensing cathode-anode pair 22, 24 will indicate the flow rate.

Figure 2:
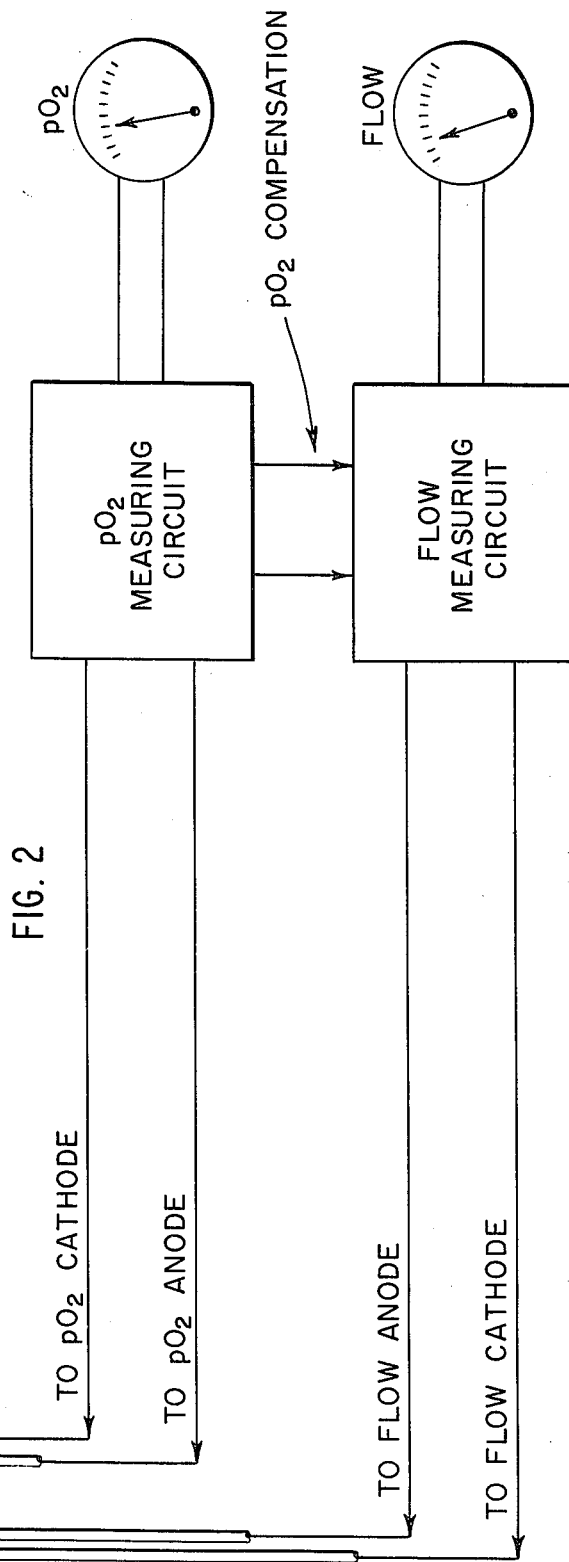
FIG. 2 is a schematic circuit diagram illustrating the measuring circuits by which flow rate and $pO_2$ may be measured with the latter measurement compensating the former.

A schematic showing of a measuring circuit arrangement is illustrated in FIG. 2. The $pO_2$ measuring circuit includes means for generating a voltage proportional to the $pO_2$ content and applying that voltage to the flow measuring circuit in a manner that varies the gain of the sensing amplifier so as to compensate for variations in the $pO_2$ value.

Tests have shown that as a voltage across the flow rate electrodes is increased the current increases up to a point at which a plateau developes, that is to say further increase in voltage produces no corresponding increase in current. The plateau current varies proportionally to the linear flow rate. From these measurements an empirical, graphical, correlation between flow velocity and plateau current can be developed. Experiments thus far indicate that the plateau current to be at about 0.4–0.9 volts.

Although this invention has been described with specific reference to oxygen sensing and flow measuring electrodes which are respectively platinum and silver/silver chloride, it will be understood that the cathode may be of any noble metal, as is well-known in the field of polarography, and the anode may be of any of a number of metals, including some giving a positive battery action. Specifically any metal that may be readily oxidized is suitable provided that for medical applications it is not toxic, and provided that it does not form a metal oxide coating that will passivate the anode surface. Preferably the anode will either be silver/silver chloride or a light metal having a high valence such as aluminum. It is also contemplated that anodes of inert metals such as platinum although requiring higher voltages, may be desirable in that they will not release metal ions into the blood stream.

The basis for flow rate measurements by the use of a polarographic cathode-anode is the provision of conditions by which the supply of oxygen to the cathode is made dependant upon the linear flow rate rather than upon the oxygen diffusion as is characteristic of classical polarography. The Clark type electrode which is optionally incorporated to sense the $pO_2$ of the medium operates accordingly to well known polarographic principles. With the small cathode surfaces and relatively large surrounding membrane, the cathode current is dependant almost entirely on the oxygen diffusion rate which in turn is proportional to the $pO_2$ of the fluid, even at very low flow rates. Diffusion of oxygen from the medium to the cathode has no appreciable affect in altering the $pO_2$ concentration in the vicinity of the membrane. The very small cathode simply does not remove sufficient oxygen to make much difference.

On the other hand the large exposed cathode used for flow rate measurements rapidly depletes the fluid near it of $pO_2$. The current plateau that is reached at these voltages represents the current necessary to deplete the medium of oxygen and establishes operating conditions wherein the plateau current is controlled by the rate at which fresh oxygen is provided at the cathode surface through the physical flow of the fluid. Practical flow rate sensing accordingly requires a cathode of relatively large area, e.g., in excess of 8 sq. mm., at an applied voltage sufficient to establish plateau current conditions. In a given system on which experiments were made at flow rates of 0. 9.9, 47 and 77 cm per second; the following measurements were made:

| Flow Rate | Current Plateau Microamperes |
| --- | --- |
| 0 | 10 |
| 9.9 | 80 |
| 47 | 220 |
| 77 | 280 |

Having thus described my invention I claim and desire to secure by Letters Patent:

1. The method of measuring the flow rate of an intravascular aqueous liquid containing dissolved oxygen comprising contacting said liquid with a polarographic cathode having a surface area greater than 8 square millimeters and with a reference anode, applying between said cathode and said anode a fixed, predetermined d.c. voltage corresponding to the characteristic plateau current of said liquid, said voltage being in the order of 0.4–0.9 volts and, while maintaining said predetermined voltage, measuring the current passing between said anode and said cathode, said current being variable as a function of the rate of flow of said liquid over a substantial range due to the substantial electrode area available to produce depletion in the adjacent volume of said liquid.

* * * * *